United States Patent [19]

Rubin

[11] Patent Number: 5,114,974

[45] Date of Patent: May 19, 1992

[54] TREATMENT OF ATHEROSCLEROSIS WITH MGNA$_2$EDTA

[76] Inventor: Martin Rubin, 3218 Pauline Dr., Chevy Chase, Md. 20815

[21] Appl. No.: 647,965

[22] Filed: Jan. 30, 1991

[51] Int. Cl.$^5$ ............................................ A61K 31/195
[52] U.S. Cl. .................................................... 514/566
[58] Field of Search ......................................... 514/566

[56] References Cited

U.S. PATENT DOCUMENTS

| | | | |
|---|---|---|---|
| 2,193,717 | 3/1940 | Faust et al. | 99/21 |
| 2,781,291 | 2/1957 | Rubin et al. | 167/68 |
| 2,846,317 | 8/1958 | Bersworth et al. | 99/182 |

OTHER PUBLICATIONS

Weiss, G. B., Drug Dev. Res. 6(2): 135–139 1985.
Bloom, S., Magnesium 5(3–4): 154–164 1986.
Des Prez, R. M. et al, Thromb Diath Haemorph 17(3–4): 516–531 1967.
Lowenhaupt, R. W. et al, J Lab Clin Med 90(1): 37–45 1977.
Orimo, H. et al, Ann NY Acad Sci 598: 444–457 1990.
Sloth–Nielsen, J. et al., Am J Surg 162 (1991); 122–125.
Proc Soc Exptl Biol and Med 103 663 (1960).
Bull Georgetown Univ Med Center 1, 33 (1951).

*Primary Examiner*—Frederick E. Waddell
*Assistant Examiner*—Diane Gardner
*Attorney, Agent, or Firm*—Lawrence I. Field

[57] ABSTRACT

The treatment of atherosclerosis by administration of pure MgNa$_2$EDTA to a patient to favorably influence one or more of the multiple stages in the complex pathophysiology of the disease.

1 Claim, No Drawings

TREATMENT OF ATHEROSCLEROSIS WITH MGNA₂EDTA

This invention relates to the treatment of atherosclerosis. More particularly it relates to the administration of a specific pure chemical compound, $MgNa_2EDTA$, to a person in order to favorably influence one or more of the multiple stages in the complex pathophysiology of atherosclerotic disease.

One object of the invention is to provide a pure, stable, non-toxic compound which upon appropriate dosage and administration to a human will enhance collateral blood flow.

Another object of the invention is the treatment of atherosclerotic disease by the intravenous infusion of pure $MgNa_2EDTA$ prepared by the interaction of $Na_2EDTA$ with suitable proportions of a specified compound of magnesium.

A further object of the invention is a treatment to reduce the level of blood plasma iron and cause its excretion in the urine.

Still a further object of the invention is to inhibit the oxidation of ascorbic acid in blood plasma by a treatment which decreases the iron content in the patient's blood plasma.

A further object of the invention is to provide a treatment which reduces the concentration of calcium in the blood plasma and causes its excretion in the urine.

A still further object of the invention is to provide a treatment to inhibit the calcium dependent coagulation process in the vascular system.

Another object of the invention is to provide a treatment to produce a flux of calcium from vascular tissue to blood plasma to urine excretions.

A further object of the invention is a treatment to enhance the vascular tissue uptake of magnesium.

An additional object of the invention is to enhance the circulation of blood in the peripheral vasculature by stimulation of the output of parathyroid hormone by the parathyroid gland.

A principal object of this invention is to provide a pure chemical compound and the method of its utilization in the human to favorably influence the multiple stages in the complex pathophysiology of atherosclerotic disease.

Atherosclerosis may be manifest by compromise of cardiac function, impairment of cerebral activity, and occlusion of blood flow which may lead to cellular death and, in the limbs, to gangrene and amputation. Its complex sequential pathology at a given anatomic site involves injury to the blood vessel wall, infiltration of the injured area by oxidized lipid laden cells, sealing of the injured area by the blood coagulation process, cellular calcium accumulation with magnesium loss, cell death with gradual occlusion of the blood vessels and compromise of the flow of blood. This may be evident by cardiac or peripheral pain on exercise. Epidemiologic studies have established that dietary control of lipid intake and changes in lifestyle such as the cessation of smoking can slow or reverse the progression of the disease and restore a state of health. Chemotherapeutic development has focused upon selective control of individual steps in the disease progression.

Deleterious lipid oxidation can occur when protective antioxidant capabilities of the vascular system are exceeded. Thus enzymatic mechanisms in plasma control the normal concentration of the potentially injurious superoxide anion free radical by its conversion to hydrogen peroxide and, in turn, to oxygen and water. In addition Vitamin E, Tocopherol, provides antioxidant protection by its presence in the cellular lipid phase. Vitamin C, Ascorbic Acid, serves this essential function in the blood plasma. However the transit of iron through the plasma from its intestinal absorption to red cell uptake for essential synthesis of hemoglobin can vitiate these protective antioxidant systems. Ferric ion in the presence of oxygen, as is normally present in blood, can catalyze the direct oxidation of lipids, Vitamin E and Vitamin C. To minimize this untoward consequence, the iron binding blood protein transferrin selectively combines with ferric ion in plasma thus decreasing the oxidative potential of the element.

In U.S. Pat. No. 2,846,317, Aug. 5, 1958 I described the utilization of sodium ethylenediaminetetraacetate, $Na_2EDTA$, and calcium disodium ethylenediaminetetraacetate, $CaNa_2EDTA$ as protective agents against the oxidation of ascorbic acid and lipids by traces of iron and other oxidative trace elements in foods. This invention has been followed since then by the annual addition to foods and vitamins of more than 100 tons of $Na_2EDTA$ for antioxidant purposes. In a subsequent publication, Rubin, M. et al. Proc. Soc. Exptl. Biol. Med. 103, 663 (1960), I reported on the in vitro characteristics of the competitive binding of iron in plasma with transferrin and added $Na_2EDTA$. Other investigators have subsequently detailed the capability of added $Na_2EDTA$ to inhibit in vitro oxidation of lipids in plasma and of ascorbic acid in defined chemical systems. The facile extension of such observations to the human system is very difficult because questions of in vivo absorption, distribution, metabolism, excretion and kinetics can exert major effects on drug pharmacology. However I have found that the intravenous administration of magnesium disodium ethylenediaminetetraacetate, $MgNa_2EDTA$, prepared and administered at the appropriate dosage in the manner to be described is capable of combining with iron in the plasma resulting in its excretion into the urine as the iron chelate. The importance of this discovery for the treatment of atherosclerotic disease is also established by epidemiologic evidence that the incidence of the disease is decreased in females during the menstrual years which are characterized by their periodic loss of blood and iron. In post menstrual years the rate of atherosclerotic disease is comparable in women and men.

Injury to the blood vessel wall can occur as a consequence of smoking, hypertension and the infiltration of oxidized lipid laden cells. When this takes place circulating blood platelets are attracted to such sites and the calcium ion dependent complex coagulation process is initiated. As it proceeds intracellular calcium ion accumulation and the loss of essential intracellular magnesium ion occurs in the infiltrated trapped cells. Upon their consequent death the local deposition of calcium and lipid provides the matrix for the formation of atherosclerotic plaque.

U.S. Pat. No. 2,193,717 in 1940 described the inhibition of the coagulation of blood in vitro by the addition of $Na_2EDTA$. My independent confirmation of this work, Bull. Georgetown University Medical Center 1, 33 (1951), established that the process depended upon the formation of the $Na_2CaEDTA$ chelate. In a series of subsequent studies it was possible to establish that the administration of $Na_2EDTA$ to animals and humans resulted in formation of the coagulation inert $Na_2Ca$-

EDTA which was rapidly excreted in the urine. The immediately available sources of the EDTA combined calcium are the blood calcium and calcium available from soft tissues. This process with its ensuing reduction in blood calcium levels has made possible the therapeutic control of this element in various pathologic situations. Thus the intravenous administration of $Na_2EDTA$ to reduce blood calcium levels in hypercalcemic states is widely utilized as accepted medical practice. The controlled intravenous administration of purified $MgNa_2EDTA$ at the appropriate dosage achieves this sam result in patients with normal blood calcium levels as well as in those with atherosclerotic disease. Thus it provides for an essential flux of calcium from sites of soft tissue deposition into the vascular system and thence into the urinary excretion in the form of the $CaNa_2EDTA$ chelate. The release of magnesium simultaneously with the induced hypocalcemia establishes an effective milieu in vitro for the uptake of magnesium by the magnesium depleted cells in atherosclerotic disease.

The gradual occlusion of blood vessels by atherosclerotic disease decreases their capacity for blood flow. This may be manifest in patients by the development of leg pain with exercise and, in extreme situations, the blockage of blood flow may finally result in gangrene with its requirement for limb amputation. These consequences in atherosclerotic disease arise from the decrease in blood oxygen delivery to tissues distal to sites of blood vessel occlusion coupled with the body's inability to efficiently remove metabolic products from such areas. Several current procedures are widely utilized to attempt to cope with this problem. Surgical removal of occluded blood vessels and their replacement by patent vessels from other anatomic sites or from donors may be undertaken. Drug therapy with aspirin may serve to inhibit the continuing coagulation process. Treatment with a drug capable of making the oxygen transporting red cell more flexible may increase its potential to pass through disease constricted blood vessels. One of the objects of this invention is to provide a pure non-toxic compound which upon appropriate dosage and administration to the human will enhance collateral blood flow.

In my U.S. Pat. No. 2,781,291 Feb. 12, 1957 I described two general procedures for the preparation of $MgNa_2EDTA$ to be utilized for the treatment of hypertension. One specifies the addition of the solution of a soluble magnesium salt such as the chloride or acetate to a molar equivalent amount of a solution of $Na_2EDTA$ while the other specifies the addition of the $Na_2EDTA$ solution to the insoluble magnesium oxide, hydroxide or carbonate. Compared to the above identified patent and for the purposes of the present invention a tenfold amount of administered $MgNa_2EDTA$ is required to obtain the presently desired therapeutic response. I have found that the second of these procedures is especially suitable for the present invention since it avoids the spontaneous formation of an insoluble dimagnesium EDTA compound, $Mg_2EDTA$, which I have identified by separation of the crystals of this product from such solutions, their characterization by X-ray analysis and determination of their elemental composition.

The preparation of the chemically pure $MgNa_2EDTA$ for the purposes of the present invention is best effected by dissolving repeatedly precipitated chemically pure EDTA in a pyrogen free aqueous solution of chemically pure sodium hydroxide containing 2 molar weights of NaOH for each molar weight of the acid. The solution of this tetraacetic acid normally will occur with agitation and gentle heating. Alternatively the solution may be prepared by dissolving chemically pure $Na_2EDTA$ in pyrogen free water. A basic magnesium compound such as the oxide or hydroxide or carbonate, in an amount providing one (1) molar weight of the magnesium compound for each molecular weight of EDTA is added to this solution. The resulting pyrogen free solution of $MgNa_2EDTA$ is then adjusted with trace amounts of an acid or base, if required, to pH 7.2 to 7.4, filtered and bottled for intravenous medical use. Freshly precipitated $Mg(OH)_2$ is particularly preferred for the preparation of $MgNa_2EDTA$ used in the present invention.

Data of the following clinical study is exemplary of the comparative pharmacologic and metabolic changes in a patient treated with a constant total amount of 245 mg of magnesium in three compositions. One consisted of 3.0 g of $MgNa_2EDTA$ as described above. The second contained 1.0 g of $MgNa_2EDTA$ with the requisite balance of Mg supplied by the addition of $MgCl_2$. The third provided the same amount of Mg as the chloride. The preparations were added to 500 ml of 5% glucose and infused during a period of three hours. They were administered intravenously to a 70 kg individual in a three hour period in random sequence with a three day rest period between treatments. The objectives of the study were to demonstrate the unambiguous physiologic and pharmacologic effects of magnesium $Na_2EDTA$ in comparison to the administration of the same amount of the element alone and to define the minimum dosage of the magnesium chelate required to initiate these changes.

TABLE 1

| | URINE IRON CONCENTRATION, ppm Change from the Initiation of Drug Infusion | | |
|---|---|---|---|
| Time | 3.0 $MgNa_2EDTA$ | 1.0 g $MgNa_2EDTA$ | $MgCl_2$ |
| 30 min. | +0.099 | +0.211 | −0.009 |
| 1 hr. | +0.697 | +0.155 | +0.080 |
| 2 hr. | — | −0.042 | +0.041 |
| 3 hr. | +0.976 | +0.059 | +0.084 |
| 4 hr. | +0.819 | +0.094 | — |
| 6 hr. | +1.183 | +0.145 | +0.055 |
| 9 hr. | +0.903 | +0.168 | +0.077 |

It is evident that the IV infusion of 3.0 g of $MgNa_2EDTA$ results in significant iron binding and enhancement in the urinary excretion of plasma iron. The 1 g dosage is threshold in its effect while the infusion of magnesium alone as $MgCl_2$ does not significantly modify urine iron excretion.

TABLE II

| | TOTAL SERUM CALCIUM, mg/dl Change from the Initiation of Drug Infusion | | |
|---|---|---|---|
| Time | 3.0 $MgNa_2EDTA$ | 1.0 g $MgNa_2EDTA$ | $MgCl_2$ |
| 30 min. | +0.4 | +0.1 | +0.3 |
| 1 hr. | 0 | −0.1 | +0.2 |
| 2 hr. | +0.1 | +0.2 | +0.1 |
| 3 hr. | 0 | +0.4 | +0.3 |
| 4 hr. | −0.5 | +0.5 | — |
| 6 hr. | −0.3 | +0.4 | +0.3 |
| 9 hr. | −0.5 | −0.3 | 0 |

By the end of the three hour IV infusion of 3.0 g $MgNa_2EDTA$ the capability for replication of serum calcium combined with the chelate and excreted into the urine has been sharply diminished. This has not occurred at the lower 1 g MgNa₂EDTA dosage where the serum calcium level is essentially the same as in the MgCl₂ control infusion.

TABLE III

IONIC SERUM CALCIUM, mg/dl
Change from the Initiation of Drug Infusion

| Time | 3.0 MgNa₂EDTA | 1.0 g MgNa₂EDTA | MgCl₂ |
|---|---|---|---|
| 30 min. | −0.55 | −0.10 | −0.11 |
| 1 hr. | −0.67 | −0.21 | −0.14 |
| 2 hr. | −0.66 | −0.23 | −0.16 |
| 3 hr. | −0.93 | −0.41 | −0.13 |
| 4 hr. | −0.65 | −0.26 | — |
| 6 hr. | −0.39 | −0.29 | +0.05 |
| 9 hr. | −0.32 | −0.09 | +0.01 |

The infusion of 3.0 g of 3.0 MgNa₂EDTA results in an immediate sharp decrease in ionized serum calcium. This reflects the rapid kinetics of Mg liberation and calcium chelation by EDTA. The process continues during the infusion. The start of the serum calcium restoration begins at the termination of the infusion. The data are completely analogous to animal and human studies of the infusion of EDTA. It is of great interest that the 1 g MgNa₂EDTA dose is clearly an initiating level for pharmacologic events. The changes with the MgCl₂ administration are minimal.

TABLE IV

URINE CALCIUM, ppm
Change from the Initiation of Drug Infusion

| Time | 3.0 MgNa₂EDTA | 1.0 g MgNa₂EDTA | MgCl₂ |
|---|---|---|---|
| 30 min. | +190 | +33 | +54 |
| 1 hr. | +945 | +34 | −21 |
| 2 hr. | +625 | +50 | −66 |
| 3 hr. | +625 | +65 | −30 |
| 4 hr. | +157 | +8 | −42 |
| 6 hr. | +82 | +29 | −34 |
| 9 hr. | +7 | +54 | −7 |

The above data establish that the systemic effect of the maximum therapeutic dosage of 3.0 g MgNa₂EDTA is sharply reflected in the urine calcium excretion. It is clear that in its passage from infusion through the vascular system into the urine MgNa₂EDTA exchanges its chelated Mg for the plasma calcium. It is of significant interest that the amount of excreted calcium is greater than the total normally circulating in the blood. Thus it is unambiguous that this treatment removes calcium from initially accessible loci in soft tissues. The process is initiated with the 1 g dosage of the drug. It does not occur by the administration of Mg++ alone.

TABLE V

SERUM PTH, C-TERMINAL, pg/ml
Change from the Initiation of Drug Infusion

| Time | 3.0 MgNa₂EDTA | 1.0 g MgNa₂EDTA | MgCl₂ |
|---|---|---|---|
| 30 min. | +150 | −50 | −20 |
| 1 hr. | +180 | −10 | −20 |
| 2 hr. | +140 | 0 | −50 |
| 3 hr. | +190 | −10 | −20 |
| 4 hr. | +180 | −40 | — |
| 6 hr. | +220 | +50 | −10 |
| 9 hr. | +160 | +100 | −30 |

The maximum therapeutic dose of 3.0 g of MgNa₂EDTA causes a rapid and protracted increase in the serum levels of C-Terminal PTH. This reflects the effect of hypocalcemia upon the release of stored PTH from the parathyroid gland and its continued elaboration and secretion. The response to the lower dose of MgNa₂EDTA is slower to be evidenced but is apparent subsequent to drug infusion. Administration of Mg++ alone is without significant effect on serum PTH.

TABLE VI

SERUM PTH, N-TERMINAL, pg/ml
Change from the Initiation of Drug Infusion

| Time | 3.0 MgNa₂EDTA | 1.0 g MgNa₂EDTA | MgCl₂ |
|---|---|---|---|
| 30 min. | +11 | −5 | (<4)* |
| 1 hr. | +14 | −3 | (<4)* |
| 2 hr. | +6 | −1 | (4)* |
| 3 hr. | +11 | −2 | +3 |
| 4 hr. | +12 | −3 | — |
| 6 hr. | +10 | −2 | +1 |
| 9 hr. | +5 | −2 | +1 |

*(measured values)

While the N-Terminal assay of PTH in this study is less definitive than that of the C-Terminal component of the hormone the stimulating effect of the 3.0 g MgNa₂EDTA dosage is evident.

TABLE VII

SERUM PHOSPHORUS, mg/ml
Change from the Initiation of Drug Infusion

| Time | 3.0 MgNa₂EDTA | 1.0 g MgNa₂EDTA | MgCl₂ |
|---|---|---|---|
| 30 min. | −0.4 | −0.4 | +0.1 |
| 1 hr. | −0.7 | −0.6 | +0.2 |
| 2 hr. | −0.8 | −0.7 | +0.3 |
| 3 hr. | −0.5 | −0.7 | +0.6 |
| 4 hr. | −0.3 | −0.5 | — |
| 6 hr. | +0.2 | −0.1 | +1.0 |
| 9 hr. | +0.5 | −0.3 | +1.5 |

The above data for both the 3.0 g and 1.0 g infusion of MgNa₂EDTA on the serum phosphorus levels, as presented above, is clearly distinguishable from the result of Mg++ administration in comparable amount. It correlates with previously reported results for serum and urine calcium as well as serum pTH changes.

TABLE VIII

SERUM MAGNESIUM, mg/dl
Change from the Initiation of Drug Infusion

| Time | 3.0 MgNa₂EDTA | 1.0 g MgNa₂EDTA | MgCl₂ |
|---|---|---|---|
| 30 min. | +0.2 | +0.2 | +0.2 |
| 1 hr. | +0.4 | +0.4 | +0.3 |
| 2 hr. | +0.6 | +0.8 | +0.6 |
| 3 hr. | +0.3 | +1.8 | +1.0 |
| 4 hr. | +0.4 | +0.9 | — |
| 6 hr. | +0.3 | +0.8 | +0.3 |
| 9 hr. | +0.6 | +0.6 | 0 |

No significant differences were noted in the urinary excretion of magnesium in the studies described above. Thus the sharp decrease in plasma magnesium at the end of the three hour infusion of 3.0 g MgNa₂EDTA compared to the second hour of the infusion period is notable. It provides support for the interpretation that a transfer of the element has occurred from plasma to the intracellular compartment of vascular cells simultaneously with the withdrawal of plasma calcium as has been previously detailed. That the release of Mg++ from EDTA chelation occurs simultaneously with the binding and urine excretion of Ca++ as the CaNa₂EDTA is further supported by the observed increase in plasma Mg++ with the administration of 1.0 g of MgNa₂EDTA. The difference compared to MgCl₂ is also evident.

TABLE IX

URINE COPPER, ppm
Change from the Initiation of Drug Infusion

| Time | 3.0 MgNa$_2$EDTA | 1.0 g MgNa$_2$EDTA | MgCl$_2$ |
|---|---|---|---|
| 30 min. | −0.004 | +0.016 | — |
| 1 hr. | +0.020 | +0.001 | — |
| 2 hr. | — | — | — |
| 3 hr. | +0.029 | — | — |
| 4 hr. | +0.037 | — | — |
| 6 hr. | +0.032 | — | (0.0005)* |
| 9 hr. | | +0.009 | +0.006 |

— not detectable
*(measured value)

The infusion of 3.0 g of MgNa$_2$EDTA results in a significant increase in urine copper excretion shortly after the initiation of drug administration. This continues through the observation period. The copper excretion at lower chelate dosage shows a modest increase compared to MgCl$_2$ administration.

TABLE X

URINE ZINC, ppm
Change from the Initiation of Drug Infusion

| Time | 3.0 MgNa$_2$EDTA | 1.0 g MgNa$_2$EDTA | MgCl$_2$ |
|---|---|---|---|
| 30 min. | +5.26 | +5.02 | −0.03 |
| 1 hr. | +27.43 | +9.10 | — |
| 2 hr. | +24.37 | +2.47 | −0.33 |
| 3 hr. | +24.37 | +7.42 | −0.40 |
| 4 hr. | +10.69 | +4.02 | — |
| 6 hr. | +12.81 | +9.40 | −0.30 |
| 9 hr. | +13.02 | +15.65 | −0.26 |

A major increase in urinary zinc excretion occurs soon after the infusion of 3.0 g of MgNa$_2$EDTA and continues throughout the treatment. At the 1.0 g dose the zinc excretion is somewhat lower but still very significant. The results are completely analogous to the infusion of both Na$_2$EDTA and CaNa$_2$EDTA as used in therapy. This supports the conclusion of the rapid in vivo exchange of relatively weakly bound Mg$^{++}$ and Ca$^{++}$ chelates compared to that of the ZnEDTA chelate.

Additional Study Observations:

Serum calcitonin was essentially unchanged and in the normal range in response to the infusion of the 1.0 g dose of MgNa$_2$EDTA and the administration of MgCl$_2$. The calcitonin concentration decreased to the lower limit of the normal range during the infusion of 3.0 g MgNa$_2$EDTA with return to normal at the end of the 3 hr. administration period. Urine manganese was significantly increased with infusion of the 3 g and 1 g doses of MgNa$_2$EDTA. There was no change in urine excretion upon administration of MgCl$_2$. The same observations were made for the urine excretion of aluminum. There were no significant concentration changes during the study in the following serum constituents either individually or comparatively: Total cholesterol; LDL cholesterol; HDL cholesterol; cortisol, insulin or glucose.

The above data demonstrates that the administration to a human of at least 1.0 g of MgNa$_2$EDTA to a maximum safe dose of 3.0 g effectively controls multiple pathophysiologic changes involved in the progression of atherosclerotic disease. This is in contrast to current drug development efforts which focus upon the control of single, though important stages of the disease pathology. Desferroxamine, for example, is a potent specific iron binding chelating compound capable of inhibiting Fe$^{+++}$ in vitro catalyzed oxidation. In experimental in vitro studies it is more potent than EDTA in inhibiting the low density lipoprotein LDL oxidation of atherosclerosis by added Fe$^{+++}$ in the presence of oxygen. In the form of its mesylate derivative it is an accepted drug to remove iron from the body in acute iron intoxication and chronic iron overload, situations in which the administration of EDTA is not clinically effective. It is potentially disadvantageous for the treatment of atherosclerosis in that it can, unlike EDTA, deplete iron from the normal binding of the element to ferritin. Likewise, unlike the administration of MgNa$_2$EDTA it is unable to cause the urinary excretion of calcium nor simultaneously provide systemic Mg$^{++}$ for the essential cellular repletion of this ion in atherosclerotic disease. It also, in contrast to the infusion of MgNa$_2$EDTA, does not have a capability to stimulate the production of PTH which can enhance the vascular flow of blood in atherosclerotic disease.

Having now described preferred embodiments of my invention it is not intended that it be limited except as it is defined in the appended claims.

I claim:

1. A method of treating atherosclerosis in a living host
    to reduce the level of blood plasma iron and cause its excretion into the urine,
    to inhibit the oxidation of ascorbic acid in blood plasma by decreasing the plasma iron content,
    to reduce the concentration of calcium in the blood plasma and cause its excretion into the urine,
    to inhibit the calcium dependent coagulation process in the vascular system,
    to produce a flux of calcium from vascular tissue to blood plasma to urine excretion,
    to enhance the vascular tissue uptake of magnesium and
    to enhance the circulation of blood in the peripheral vasculature by stimulation of the output of parathyroid gland
    which treatment comprises the intravenous infusion of pure disodium salt of the Mg chelate of EDTA (Na$_2$MgEDTA) prepared by the interaction of Na$_2$EDTA with a compound of magnesium selected from the group consisting of MgO, Mg(OH)$_2$ and MgCO$_3$, in a dosage of at least 1.0 g and not more than 3.0 g over a three hour interval.

* * * * *